United States Patent [19]

May

[11] 4,058,123
[45] Nov. 15, 1977

[54] COMBINED IRRIGATOR AND EVACUATOR FOR CLOSED WOUNDS

[75] Inventor: Edwin A. May, Ridgewood, N.J.

[73] Assignee: International Paper Company, New York, N.Y.

[21] Appl. No.: 618,482

[22] Filed: Oct. 1, 1975

[51] Int. Cl.[2] .............................................. A61F 5/44
[52] U.S. Cl. .................................. 128/278; 128/240; 128/DIG. 12
[58] Field of Search .................. 128/276, 278, 214 D, 128/214 B, 214 F, 2 F, 240, 248, 251, DIG. 12; 137/565, 564.5, 565.1, 565.2; 222/94, 96, 209, 212, 213, 386.5

[56] References Cited

U.S. PATENT DOCUMENTS

| | | | |
|---|---|---|---|
| 1,245,845 | 11/1917 | White | 128/278 |
| 2,074,223 | 3/1937 | Horiuchi | 128/DIG. 12 |
| 3,115,138 | 7/1960 | McElvenny et al. | 128/278 |
| 3,291,151 | 12/1966 | Loken | 128/124 B |
| 3,398,743 | 8/1968 | Shalit | 128/240 |
| 3,572,340 | 3/1971 | Lloyd et al. | 128/278 |
| 3,592,365 | 7/1971 | Schwartzman | 222/209 |
| 3,774,611 | 6/1972 | Tussey et al. | 128/278 |
| 3,779,243 | 12/1973 | Tussey et al. | 128/278 |
| 3,782,384 | 1/1974 | Timmermans | 128/277 |
| 3,809,086 | 5/1974 | Schachet et al. | 128/278 |

OTHER PUBLICATIONS

"A New Approach to Chronic Osteomyelitis" by Goldman et al., Orthopedics, Apr. 1960, pp. 63.
"Treatment of Osteomyelits–"by Edward Compere (1962).

*Primary Examiner*—Robert W. Michell
*Assistant Examiner*—Henry S. Layton
*Attorney, Agent, or Firm*—Finnegan, Henderson, Farabow & Garrett

[57] ABSTRACT

A self-contained, combined irrigator and evacuator for closed wounds comprising a housing divided into two sections by a biased divider so that movement of the divider in one direction causes pumping of fluid from one section to a patient for wound irrigation while simultaneously effecting evacuation of fluid from the wound site and collection of the evacuated fluid in the second section.

19 Claims, 6 Drawing Figures

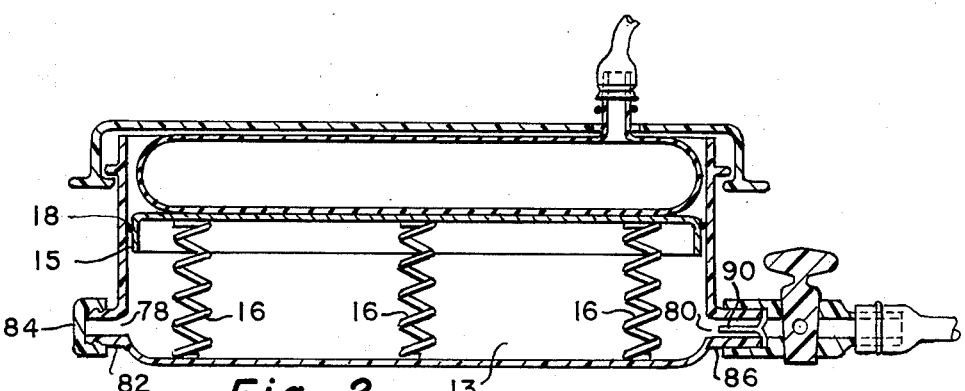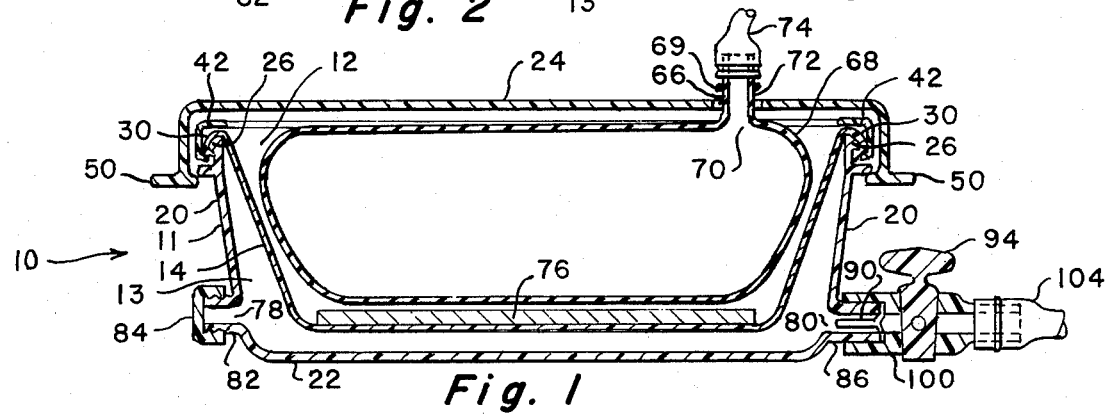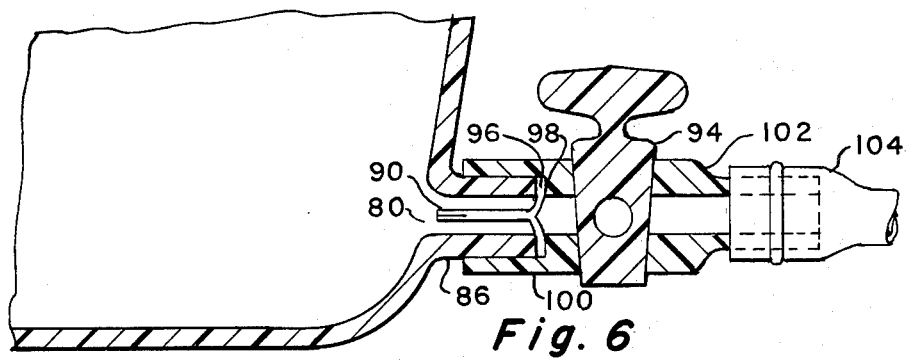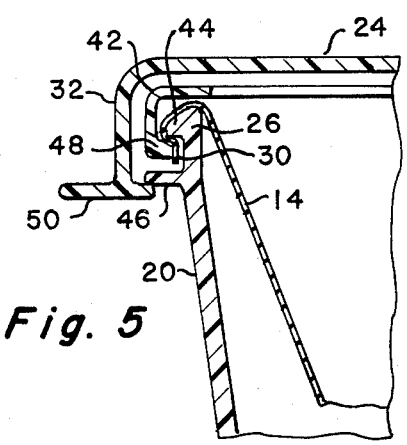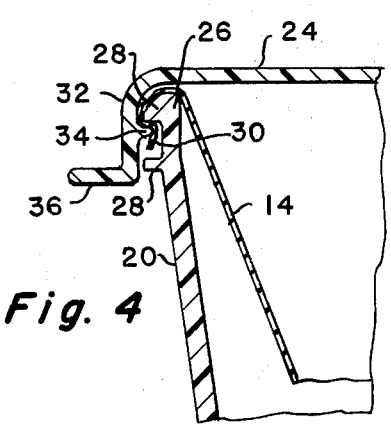

COMBINED IRRIGATOR AND EVACUATOR FOR CLOSED WOUNDS

BACKGROUND OF THE INVENTION

Field of the Invention

This invention relates to medical apparatus for cleansing internal wounds; more particularly, it relates to a self-contained, disposable, portable, combined wound irrigator and evacuator.

The evacuation of fluids from a closed wound is a common medical practice. This is often done on completion of surgery. Fluid evacuation usually is accomplished through gravity drainage, pressure dressings or compression bandages or by negative pressure or suction, the latter being preferred. Conventional closed wound suction devices include power driven vaccum pumps, central suction systems, or evacuated bottles. While each of these evacuation systems effectively evacuate a wound, all except the evacuated bottles have many disadvantages because of their cost, noise and restriction on patient mobility resulting in the retardation of post-operative exercises, ambulation and rehabilitation. The evacuated bottle may provide mobility but has the disadvantages of cost and the necessity of having to have many available since when one bottle fills it must be replaced. The filled bottle must be emptied, sterilized and re-evacuated.

In addition to evacuating fluids from a closed wound, it is frequently necessary to expose the wound site to a flow of an irrigating solution to bathe the infected area. This has been particularly true in the case of chronic osteomyelitis. In the past, wound bathing has generally been accomplished by means of gravitational flow, such as through an intraveneous device. Irrigation in this manner further restricts patient mobility.

The frequent necessity of bathing and evacuating a wound site has accentuated the need for a device which will eliminate the cumbersome, complicated, expensive and restrictive combination of irrigation equipment and evacuation equipment.

The disadvantages of the previous wound evacuation systems have, in part, been overcome by recent inventions such as those shown in U.S. Pat. Nos. 3,774,611 and 3,779,243. In both of these devices the evacuator comprises an evacuation chamber formed with resilient side walls which, after manual compression and release, tend to return to their original position. During return to their original position, they provide a reduced pressure on the interior of the container which, when connected to an internal wound by means of a catheter tube, effects evacuation of the wound. While these inventions overcome the serious disadvantages of power-driven vacuum pumps and central suction systems, they have their own disadvantages. Their major disadvantage is the possibility of accidental compression of the container at a time when it is undesirable.

Another disadvantage includes the necessity of inverting the container and compressing it to empty for reuse since this may disturb the patient. Furthermore, these devcies are deficient in that they serve only one purpose, namely the removal of fluids from the wound. Thus, although these evacuation devices permit a certain amount of patient mobility, if wound irrigation is also necessary, the patient must be connected to a means for irrigating the wound, such as an intraveneous device. The necessity of combining the two systems, one for evacuation and one for irrigation, makes the entire system inconvenient, relatively expensive and cumbersome. While ostensibly a patient could be ambulatory by carrying an intraveneous bottle of irrigating fluid above his head and carrying or wearing an evacuator device, it is unlikely that such a situation would be considered a convenient solution.

It is the disadvantages of the prior art with respect to mobility, expense, convenience, disposability, safety and utility that the present invention is intended to overcome.

BRIEF DESCRIPTION OF THE INVENTION

In accordance with the invention, as embodied and broadly described herein, the combined wound irrigator and evacuator comprises a rigid housing forming a chamber, means under bias for dividing the chamber into a pressure-irrigating section and a suction-evacuating section, means for preventing fluid flow between the sections, and access means providing fluid flow access to irrigating and evacuating sections.

With the chamber dividing means depressed, against bias, the increased volume of the irrigating section is filled with an irrigating solution and the bias or resiliency of the dividing means tends to expel the solution through the access means.

Releasing the irrigating solution from the irrigating section permits the chamber dividing means to return under bias to its original position which automatically provides a reduced pressure in the evacuating section. The suction in the evacuating section is transmitted to the wound through the access means of the evacuating section and a fluid conduit means.

It is preferred that the dividing means be a resilient diaphragm secured at its edges to the housing such that fluid flow between the sections is prevented. The diaphragm may be secured to the housing by locking the edges of the diaphragm between the side walls of the housing and the cover. In the preferred embodiment, the overlapping edges of the diaphragm are secured to the rim of the side walls by a diaphragm retaining ring so that the diaphragm acts as a fluid seal between the sections; the retaining ring also permits the removal of the cover without affecting the attachment of the diaphragm.

Flow of fluid, be it irrigating fluid, aspirated fluid or air, into and out of the sections of the irrigator and evacuator must be controlled. Therefore, the flow control means are provided for each of the access means. The flow control means must permit the selective introduction and selective expulsion of fluid from the irrigating section and from the evacuating section.

In the preferred embodiment, the inlet opening of the evacuating section has a check valve which permits introduction but prevents expulsion of fluid from the evacuating section through the inlet. It may be desirable to include on the inlet opening of the evacuating section a manually controlled valve in conjunction with the one-way check valve. This design would preserve the vacuum created in the evacuating section so that the irrigator and evacuator could be prepared in advance and set aside for use. Also in the preferred embodiment, the outlet opening of the evacuating section includes a removable cap.

The preferred embodiment includes a flexible bag containing an irrigating solution and means through which the solution can be expelled. The bag is placed on the diaphragm and the cover, when fitted onto the base, causing the bag to depress the diaphragm, making the irrigator and evacuator ready for use.

It is also preferred that a rigid plate be placed over a substantial portion of the irrigating section side of the diaphragm to facilitate uniform distribution of force and displacement of the diaphragm when the diaphragm is depressed.

The embodiments described each meet the objective of providing an inexpensive, reliable, disposable or reusable, portable, self-contained combined irrigator and evacuator.

Additional objectives and advantages of the invention will be set forth in part in the description which follows, and, in part, will be obvious from the description, or may be learned by practice of the invention. The objectives and advantages of the invention may be realized and obtained by means of instrumentalities and combinations particularly pointed out in the appended claims.

The invention consists of novel parts, constructions, arrangements, combinations and improvements shown and described. The accompanying drawings, which are incorporated in and constitute a part of the specification, illustrate an embodiment of the invention and, together with the description, serve to explain the principles of the invention.

BRIEF DESCRIPTION OF THE DRAWINGS

FIG. 1 is a sectional view of a combined wound irrigator and evacuator formed in accordance with the preferred embodiment of this invention.

FIG. 2 is a sectional view of a second embodiment of the invention.

FIG. 4 is a magnified sectional view of the diaphragm attachment means of the embodiment of FIG. 3.

FIG. 5 is a magnified sectional view of the diaphragm attachment means of the preferred embodiment of FIG. 1.

FIG. 6 is a magnified sectional view of the flow control means on the inlet port of the evacuating section of the preferred embodiment of FIG. 1.

DETAILED DESCRIPTION OF THE PREFERRED EMBODIMENT

Figure 3:
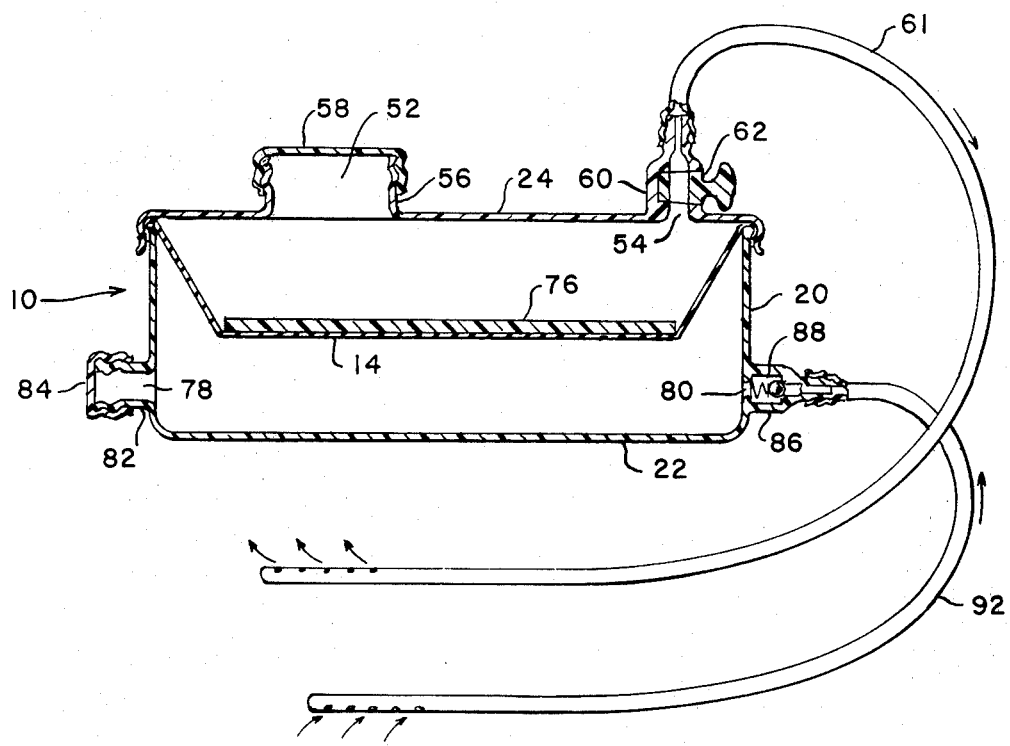
FIG. 3 is a sectional view of a third embodiment of the invention.

Reference will now be made in detail to the present preferred embodiment of the invention, an example of which is illustrated in FIG. 1.

The combined irrigator and evacuator of the invention permits bathing of a closed wound with an irrigating solution while simultaneously removing and collecting fluid from the closed wound. This is accomplished by utilizing a biased divider forming two sealed sections in a chamber. As fluid is expelled from one section to the wound by the force of the biased divider, negative pressure is created in the other section which, when communicated to the closed wound, aspirates fluid from the wound and collects it in the latter section.

As is seen in FIG. 1, a combined irrigator and evacuator 10 formed in accordance with this invention comprises a rigid housing 11 forming a chamber. Means under bias is provided for dividing the chamber into two sections namely, a pressure-irrigating section 12 and a suction-evacuating section 13. The dividing means, which in the preferred embodiment of FIG. 1 is a diaphragm 14, is biased toward the upper position in the chamber. The bias in the preferred embodiment is provided by the resiliency of the diaphragm 14.

Alternatively, the chamber may be divided by a piston 15 as shown in FIG. 2. In such a case, the bias could be supplied by springs, such as compression springs, 16 located in the evacuating section 13.

References to positions as top or bottom, left or right are used for ease in description of the illustrated embodiments and are not intended as terms of limitation.

It is, of course, necessary that fluid communication between the pressure-irrigating section 12 and the suction-evacuating section 13 be prevented. When the dividing means is a diaphragm 14 as in the preferred embodiment, fluid flow between the sections is prevented by securely attaching the diaphragm around its entire periphery to the housing 11. In the embodiment of FIG. 2 having a piston 15 as a dividing means, some form of conventional movable peripheral seal, such as a piston ring 18, would be necessary to prevent fluid flow between the sections.

It is preferred that in the embodiments of FIGS. 1, 2 and 3, the rigid housing 11 consist of a base having side walls 20 and a bottom or end wall 22 and a cover 24 forming a top or end wall.

In one embodiment, the diaphragm 14 may be securely attached to the housing 11 by overlapping the rim 26 of the side walls 20 and being clamped to the side walls 20 by the cover 24. The embodiment of FIG. 3 illustrates this method of attaching the diaphragm 14.

FIG. 4 provides a more detailed illustration of the method of attaching the diaphragm 14 in FIG. 3. The side walls 20 include, near the rim 26, a plurality of outwardly projecting, vertically-spaced, ribs 28. The edge 30 of the diaphragm 14 overlaps at least one of the outwardly projecting ribs 28. The cover 24 includes a downward projecting flange 32 about its perimeter. The inside surfaces of the flange include one or more inwardly projecting ribs 34 which, when the cover 24 is placed over the base, engage the outwardly projecting ribs 28 on the rim 26 of the side walls 20. The edge 30 of the diaphragm 14 is clamped between the engaged ribs 28 and 34, thereby securely attaching the diaphragm 14 and preventing fluid flow between the sections 12, 13. As seen in FIG. 4, extending outwardly from the end of the flange 32 of the cover 24 is another flange 36 provided to be used as a handle for installing and removing the cover 24 from the base.

In the preferred embodiment, FIG. 1, the diaphragm 14 is securely attached to the side walls 20 by clamping the overlapping edge 30 of the diaphragm 14 between the rim 26 of the side wall 20 and a diaphragm retaining ring 42. A magnified view of the attachment of the diaphragm 12 in the preferred embodiment is illustrated in FIG. 5. The side walls 20 include an outwardly projecting shoulder 44 at the rim 26. Also included on the side walls 20 is an outwardly projecting flange 46 which is vertically-spaced below the shoulder 44. The edge 30 of the diaphragm 12 overlaps the shoulder 44. An annular diaphragm retaining ring 42, the cross-section of which is essentially cup-shaped with an inward projecting rib 48 at one end, is placed over the rim 26 of the side walls 20 and the overlapping edge 30 of the diaphragm 14. The rib 48 engages the shoulder 44 thereby securely attaching the retaining ring 42 and the diaphragm 14 to the side walls 20.

The cover 24 includes a downward flange 32 which includes a horizontal member 50 at its end forming an inverted T. The Inward projecting portion of the horizontal member 50 engages the outwardly projecting flange 46 of the side wall 20 to securely attach the cover 24 to the base. The outward extending portion of the horizontal member 50 acts as a handle for installing and removing the cover 24. The particular advantage of this method of attaching the diaphragm 14 to the side walls 20 is that the cover 24 may be removed from the base without affecting the attachment of the diaphragm 14.

In accordance with the invention, access means are provided to each of the sections 12, 13. At a minimum, one access means must be provided to each of the sections. It is preferred, however, that the evacuating section 13 have two openings, one for introducing fluid into the section and one for expelling fluid from the section. Access to the irrigating section 12 may consist of two openings, one for introducing fluid to the section and one for expelling fluid from the section as seen in FIG. 3; however, it is preferred that only one opening be provided for access to the irrigating section.

It also is preferred that each opening to the sections 12, 13 have means for controlling fluid flow through the openings. In the embodiment illustrated by FIG. 3, there are two openings to each section. The cover 24 includes an inlet opening 52 and an outlet opening 54. Formed in the cover 24 about the inlet opening 52 is an outwardly projecting tubular extension 56 on which is mounted a removable cap 58. The diameter of the inlet opening 52 is sufficiently large to provide access to the diaphragm in order to permit depressing the diaphragm 14 prior to introducing irrigation fluid. Once the fluid is introduced into the irrigating section, the cap 58 is placed over the opening 52.

A more automated version of the wound irrigator and evacuator can be made by forming the inlet opening 52 such that it can be connected to a pressurized filling device (not shown). Filling of the irrigating section 12 with irrigating fluid under pressure will depress the diaphragm 14 and will obviate the necessity of depressing the diaphragm 14 by some outside force means, such as manually.

Further in accordance with this invention, the irrigating section outlet opening 54 is provided with fluid flow control means. For example, as is shown in FIG. 3, the irrigating section outlet opening 54 is ringed by an outwardly projecting tubular extension 60, which may be formed as an integral part of the cover 24. The extension 60 includes a portion adapted to receive a conduit, such as a conventional catheter 61. The catheter 61 conducts the irrigating fluid forced from the irrigating section 12 by the diaphragm 14 to the wound. The tubular extension 60 also is provided with a stop-cock valve 62 for controlling fluid flow through the outlet opening 54. During and after filling of the irrigating section 12, the stop-cock valve 62 is closed, and it is only opened when properly connected to a wound.

While a stop-cock valve 62 is depicted in this embodiment, any convenient means of selectively permitting and preventing fluid flow from the irrigating section 12 may be used. The catheter 61 may be directly connected to the outlet opening 54 and a conventional hose clamp or conventional intraveneous set control (not shown) may be used to control flow from the irrigating section. This, of course, requires continuous attachment of the catheter 61 which may be undesirable if the irrigator and evacuator 10 is to be filled and set aside for future use.

In the preferred embodiment illustrated in FIG. 1, the cover 24 has only one opening 66 for access to the irrigating section 12.

Irrigating solution, in the preferred embodiment, is contained in a flexible plastic solution bag 68 which has one opening 70 from which extends a tubular extension 72. The bag 68, filled with irrigating solution, is placed in the irrigating section 12 by removing the cover 24 and placing the bag 68 on the diaphragm 14 which remains attached to the base due to the diaphragm retaining ring 42. The cover 24 is placed over the bag 68 with the tubular extension 72 from the opening 70 in the bag 68 passing through the opening 66 in the cover 24. Fluid flow from the bag 68 is prevented by any convenient means, such as a conventional clamp 69 on the tubular extension 72. The filled bag 68 is then forced down by pressing down on the cover 24 to attach it to the base. Forcing down the filled bag 68 causes depression of the diaphragm 14. Once the cover 24 is attached to the base, the irrigator and evacuator is ready to be connected to a wound.

A fluid conduit means 74, such as a catheter, may be attached to the tubular extension 72 from the bag 68. It may be preferred, however, that the tubular extension 72 from the bag be a continuous fluid conduit means having a plurality of apertures remote from the bag for fluid flow communication to the wound thus making unnecessary the fluid conduit means 74 clamped to the tubular extension 72.

The flexible plastic bag 68 may be reuseable. It, of course, would require sterilization and refilling. Another opening with an appropriate flow control means may be provided in the bag 68 to permit refilling.

It is preferred that, where the dividing means is a diaphragm 14, as in FIG. 1, a rigid plate 76 cover a substantial portion of the center of the irrigating section side of the diaphragm 14. The plate 76 will provide some rigidity to the diaphragm to facilitate uniform displacement and force distribution whether depressed by manual force, fluid pressure or the filled solution bag 68.

Preferably, two openings are formed into the base for access to the evacuating section 13. As seen is FIGS. 1, 2 and 3, an outlet opening 78 and an inlet opening 80 are formed into the base. When the diaphragm 14 is depressed, the fluid in the evacuating section 13, whether liquid aspirated from a wound or air, must be expelled. The outlet opening 78 provides a means for expelling that fluid. It also provides the added advantage that the irrigator and evacuator 10 need not be inverted to empty before reuse.

A tubular extension 82 is formed in the base around the outlet opening 78. The tubular extension provides a means for mounting a removable cap 84. Any suitable means, including a valve, for selectively opening and closing the outlet opening 78 is acceptable. The opening 78 must be sealed after the evacuating section 13 is emptied in order to preserve the negative pressure which will be created as the dividing means returns to its original position.

The inlet opening 80 to the evacuating section 13 provides a means for admitting fluid aspirated from a wound to the evacuating section. A tubular extension 86 is formed into the base around the opening 80. Mounted within the tubular extension is a one-way flow control means which permits fluid aspirated from a wound to enter the evacuating section but prevents such fluid from being expelled through the opening 80 and possibly returning to the wound from which is was aspirated. The one-way flow control means may be a ball-check valve 88, as seen in FIG. 3, and elastomeric flutter valve 90, as in FIGS. 1 and 6, a molded non-reflex valve, or any other convenient means of achieving one-way flow control.

It is preferred that a flow control means which can completely prevent flow through the inlet opening 80 be mounted in the fluid flow communication with the inlet opening 80. This is preferable when the irrigator and evacuator 10 is to be prepared and set aside for future use. In order to preserve the partial vacuum in the evacuating section 13 until ready for use, the inlet opening 80 must be completely obturated. This may be accomplished by clamping shut a fluid conduit means, such as the catheter 92 (FIG. 3) which is mounted in fluid flow communication with the tubular extension 86 from the inlet opening 80.

In the preferred embodiment, FIG. 1, the flow control means on the inlet opening 80 to the evacuating section 13 includes an elastomeric flutter valve 90 and a stop-cock valve 94. A magnified view of the inlet opening 80 and flow control means is illustrated in FIG. 6.

In FIG. 6 it may be seen that the elastomeric flutter valve 90 is located within the tubular extension 86 formed into the side wall 20 around the inlet opening 80. The flutter valve is clamped in place at its spread end 96 between the end of the tubular extension 86 and a step 98 formed into the inside surface of a sleeve 100 placed around the tubular extension 86. The sleeve 100 provides a means for mounting the stop-cock valve 94 in the line of fluid flow to the inlet opening 50. The stop-cock valve 94 is depicted in the closed position. The end of the sleeve 100 remote from the inlet opening 80 is formed into a neck 102 for fluid flow connection with a fluid conduit means, such as catheter 104. With the stop-cock valve 94 open, negative pressure in the evacuating section 13 is transmitted to the wound via the fluid conduit means 104 and fluid thereby aspirated from the wound is conducted to the evacuating section, passing through the fluid conduit means 104, the stop-cock valve 94 and the elastomeric flutter valve 90.

It is preferred that the component parts of the irrigator and evacuator 10 be made of inexpensive material which, of course, is non-reactive with medicinal preparations and body fluids and is non-toxic. While the use of such material is to make the irrigator and evacuator inexpensive enough to be disposable, the irrigator and evacuator 10 may be reused and, therefore it may be preferred to construct it of material which can be sterilized.

The container is designed so that it can be molded easily from any suitable thermoplastic or thermosetting material, such as polystyrene, polycarbonate, polyethylene or polypropylene. The diaphragm can be made of natural rubber or a synthetic material, for example neoprene or butyl rubber.

The irrigating solution used, whether poured, pressure filled, or contained in a flexible bag, may be one of any number of medicinally acceptable fluids. Examples of such irrigating fluids are sterile, normal saline solutions with or without an antibiotic, a penicillin detergent solution, or a currently-marketed brand of irrigating fluid such as American Cyanamids' "Aerosol Wash."

The ease of use of the irrigator-evacuator becomes obvious through a description of the preparation and operation of the preferred embodiment (FIG. 1).

To prepare the irrigator and evacuator for use, the cover 24 is removed from the base. A filled solution bag 68 is placed on the rigid plate 76 on the center of the diaphragm 14. The cover 24 is placed over the solution bag 68 and the tubular extension 72 from the opening 70 in the bag is passed through the opening 66 in the cover 24. Of course, the clamp 69 closing the extension 72 is closed. The cap 84 is removed from the evacuating section outlet opening 78 and the cover 24 is pressed down, until the flange 50 engages the rib 46 to lock the cover 24 to the base. The filled bag 68 causes the diaphragm 14 to be depressed expelling the fluid in the evacuating section 13 through the outlet opening 78. With the cover 24 locked in place, the cap 84 is placed over the outlet opening 78 and the stop-cock valve 94 at the evacuating section inlet opening 80 is closed. In this condition, the irrigator and evacuator is ready for use.

To use, one end of a catheter is connected to the bag's tubular extension 72 and the other end of the catheter is placed in fluid flow communication with the closed wound. A second catheter is connected to the neck 102 of the sleeve 100 over the evacuating inlet opening 80 and the remote end of the second catheter is placed in fluid flow control means, for example by opening the clamp 69 which prevents the fluid from leaving the solution bag 68 and by opening the stop-cock valve 94, the fluid will be expelled from the irrigating section 12 by the diaphragm 14 as it moves upward to return to its normal, unstretched position. As the volume of the evacuating section 13 increases, the pressure therein is reduced and fluid is aspirated from the closed wound to the evacuating section. The irrigation and evacuation will continue until the diaphragm 14 returns to its rest position.

It may be preferred to control the rate of irrigation fluid flow. This can be accomplished by placing a conventional intraveneous set control on the catheter from the irrigating section. As the rate of irrigating fluid flow is directly related to the rate of aspitation of fluid, providing a set control also prevents the development of excessive negative pressure in the evacuating section.

The preferred embodiment of the irrigator and evacuator may be reused. To do so, it is necessary to disconnect the irrigating catheter and to close the stop-cock valve 94. On removing the cover 24, discarding the empty solution bag 68 and replacing it with a filled bag 68 and placing the cover 24 over the bag, the evacuating section 13 is ready to be emptied and refilled. Placing the outlet port 78 over an appropriate container, removing the cap 84, and pressing down on the cover 24 will expel the evacuated fluid in the evacuating section 13 and prepare the irrigator and evacuator for use. Connecting the irrigating catheter, replacing the cap 84 on the outlet opening 78, opening the stop-cock valve 94, and removing the clamp from the tubular extension 72 of the solution bag 68 will commence simultaneous irrigation and evacuation for another cycle.

The irrigator and evacuator need not be reused. It may be removed from the patient and replaced with another, previously prepared irrigator and evacuator. The used one may be discarded or emptied and sterilized for reuse at a later time.

One of the advantages of the irrigator-evacuator as here embodied is its compactness, independence from outside power or vacuum sources and gravity draining bottles of irrigating fluid, and its resulting portability. Should irrigation and evacuation be desirable on a wound of an ambulatory patient, it is possible to provide a means for carrying the irrigator-evacuator such as a shoulder strap or a belt attached to the side walls 20. This provides a means of carrying the irrigator-evacuator and thus facilitates continuous irrigation and evacuation of a wound in an ambulatory patient.

While the preferred embodiment of the invention has been illustrated and described, it will be appreciated by those skilled in the art and others that various changes can be made therein without departing from the spirit and scope of the invention. Hence, the invention can be practiced otherwise than specifically described herein.

What is claimed is:

1. A combined irrigator and evacuator for use in bathing a wound with an irrigating solution and removing fluid from the wound, comprising:
    a. a rigid housing forming a chamber;
    b. means under bias for dividing said chamber into a pressure-irrigating section and a suction-evacuating section, said bias tending to reduce the volume of said pressure-irrigating section and increase the volume of said suction-evacuating section;
    c. seal means for preventing fluid flow between said pressure-irrigating section and said suction-evacuating section;
    d. access means providing fluid flow access to said sections; and
    e. means in said pressure-irrigating section for containing said irrigating solution.

2. The combined irrigator and evacuator as in claim 1 wherein said access means comprises an opening in fluid flow communication with said pressure-irrigating section and an opening in fluid flow communication with said suction-evacuating section, wherein said opening to said suction-evacuating section has an outwardly projecting tubular extension to permit connection in fluid flow communication with a fluid conduit means, and wherein said irrigating solution containing means has an opening in fluid flow communication through the opening to said pressure-irrigating section through which said solution can be expelled.

3. The combined irrigator and evacuator as in claim 2 wherein said opening to said suction-evacuating section includes a flow control means which permits the selective opening and closing of said opening.

4. The combined irrigator and evacuator as in claim 2 wherein said irrigating solution containing means is a flexible bag in said irrigating section.

5. The combined irrigator and evacuator as in claim 4 wherein said flexible bag includes a tubular extension projecting outwardly from an opening in said bag, said extension being placed through said access means to said irrigating section for connection to a fluid conduit means, the inclusion of said bag filled with said irrigating solution in said irrigating section displacing the chamber dividing means against bias thereby increasing the volume of said irrigating section and decreasing the volume of said evacuating section, the bias of said chamber dividing means tending to expel said irrigating solution from said bag through said tubular extension and increasing the volume of said evacuating section creating a suction pressure in said evacuating section.

6. The combined irrigator and evacuator as in claim 5 wherein said tubular extension from said solution bag is a continuous tube having apertures through the remote end thereof for conducting the solution from said bag to said wound, said tube being passed through said access means to said irrigating section and the remote end being placed in fluid flow communication with the wound.

7. A combined irrigator and evacuator for use in bathing a wound with an irrigating solution and removing fluid from the wound, comprising:
    a. a rigid housing forming a chamber;
    b. a planar, resilient diaphragm for dividing said chamber into a pressure-irrigating section and a suction-evacuating section, said diaphragm being secured at its edges to said housing such that fluid flow between said sections is prevented;
    c. access means providing fluid flow access to said sections;
    d. flow control means permitting selective opening and closing of said access means; and
    e. means in said pressure-irrigating section for containing said irrigating solution, said means having an opening in fluid flow communication through the access means to said pressure-irrigating section through which said solution can be expelled.

8. The combined irrigator and evacuator as in claim 7 wherein said rigid housing consists of a base having a rim and a cover having a top wall which is adapted to be mounted on said base forming a chamber and wherein the edges of said diaphragm overlap said side walls and are secured to said side walls by said cover, said diaphragm preventing fluid flow between said sections.

9. The combined irrigator and evacuator as in claim 8 wherein a diaphragm retaining ring is included on the rim of said side walls for securing the edges of said diaphragm to the rim of said side walls preventing a fluid flow seal between said sections and permitting removal of said cover without affecting attachment of said diaphragm.

10. The combined irrigator and evacuator as in claim 8 wherein said side walls include a plurality of vertically spaced outwardly protruding ribs near the rim of said side walls over which the overlapping edges of said diaphragm extend and wherein said cover has a downwardly extending flange at its edges having an inwardly projecting rib which engages the outwardly projecting ribs of said one side walls to lock the overlapping edges of said diaphragm between said cover and said side walls and to securely attach said cover to said base.

11. The combined irrigator and evacuator as in claim 7 wherein said access means includes at least one port providing fluid flow communication with said irrigating section and includes an inlet port and an outlet port providing fluid flow communication with said evacuating section, and wherein each of said inlet and outlet ports includes a flow control means to permit selective opening and closing of said ports.

12. The combined irrigator and evacuator as in claim 11 wherein said evacuating section inlet port has means for receiving fluid conduit means in fluid flow communication.

13. The combined irrigator and evacuator as in claim 11 wherein said flow control means on said evacuating section outlet port is a removable cap, and wherein said flow control means on said evacuating section inlet port permits fluid flow into said evacuating section and prevents expulsion of fluid from said section through said inlet port.

14. The combined irrigator and evacuator as in claim 13 wherein said flow control means on said evacuating section inlet port includes a check valve and a shut-off valve.

15. A combined irrigator and evacuator for use in bathing a wound with an irrigating solution and removing fluid from the wound, comprising:
   a. a rigid housing forming a chamber;
   b. a resilient diaphragm for dividing said chamber into a pressure-irrigating section and a suction-evacuating section, said diaphragm being secured at its edges to said housing such that fluid flow between said sections is prevented;
   c. access means providing fluid flow access to said sections;
   d. a flexible bag in said pressure-irrigating section, said bag containing an irrigating solution and having a means through which said solution can be expelled; and
   e. a flow control means for selectively permitting and preventing fluid flow through said access means.

16. The combined irrigator and evacuator as in claim 15 wherein said flexible bag includes a tubular extension projecting outwardly from an opening in said bag and includes a means for selectively obturating fluid flow through said tubular extension, said extension being placed through said access means to said irrigating section for connection to a fluid conduit means, the inclusion of said bag in said irrigating section displacing said diaphragm thereby increasing the volume of said irrigating section and decreasing the volume of said evacuating section, the resiliency of said diaphragm tending to expel said irrigating solution from said bag through said tubular extension and increasing the volume of said evacuating section creating a suction pressure in said evacuating section.

17. A combined irrigator and evacuator for simultaneously bathing a wound with an irrigating fluid and removing fluids from the wound, comprising:
   a. a rigid housing consisting of a base having a first end wall and side walls and a cover having a second end wall which is adapted to be mounted on said base forming a chamber therein, said cover having an opening;
   b. a resilient diaphragm dividing said chamber into an irrigating section between one of said end walls, and said diaphragm and an evacuating section between said diaphragm and the other of said end walls, the edges of said diaphragm overlapping said side walls;
   c. a diaphragm retaining ring, the perimeter of which overlaps said side walls such that the overlapping edges of said diaphragm are securely locked between said retaining ring and said side walls thereby preventing fluid flow between said irrigating and evacuating sections, said diaphragm retaining ring being mounted to said side walls permitting the removal of said cover without affecting the attachment of said diaphragm to said side walls;
   d. a flexible bag containing irrigating solution in said irrigating section, said bag having a tubular extension projecting outwardly through said opening in said cover for connection to a fluid conduit means and including a means for obturating fluid flow through said extension, the inclusion of said bag in said irrigating section stretching said diaphragm;
   e. an inlet and an outlet opening through said housing communicating with said evacuating section;
   f. an outwardly extending tubular extension from said inlet for connection to a fluid conduit means and one-way flow control means to permit introduction of fluid into said evacuating section through said inlet and preventing expulsion of fluid from said evacuating section through said inlet; and
   g. a removable cap adapted to be placed on the outlet to selectively permit expulsion of fluid from said evacuating section.

18. The combined irrigator and evacuator as in claim 17 wherein said tubular extension from said flexible plastic bag is a continuous tube having apertures at the remote end thereof for conducting solution from said bag to said wound, and wherein a flow control means is mounted on said tube to control flow through said tube.

19. The combined irrigator and evacuator as in claim 18 wherein said one-way flow control means also includes a shut-off valve.

* * * * *